United States Patent
Ryan et al.

(10) Patent No.: US 8,080,204 B2
(45) Date of Patent: Dec. 20, 2011

(54) TWO DIMENSIONAL SAMPLE HANDLER

(75) Inventors: Dale Ryan, Fairport, NY (US);
Johannes Porte, Fairport, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 13/004,403

(22) Filed: Jan. 11, 2011

(65) Prior Publication Data

US 2011/0104008 A1 May 5, 2011

Related U.S. Application Data

(62) Division of application No. 11/672,614, filed on Feb. 8, 2007, now Pat. No. 7,867,768.

(51) Int. Cl.
*G01N 35/04* (2006.01)

(52) U.S. Cl. ............... 422/65; 422/63; 436/47; 436/48; 436/49; 198/345.1; 198/465.1; 198/468.01

(58) Field of Classification Search .................. None
See application file for complete search history.

*Primary Examiner* — P. Kathryn Wright
(74) *Attorney, Agent, or Firm* — Todd J. Burns

(57) ABSTRACT

A method for positioning a sample in a diagnostic analyzer includes: providing two or more sample carriers on a conveyor; providing a fixed registration element for each sample carrier at predetermined locations along the conveyor; providing a flexure device positioned between the sample carrier and the conveyor; advancing the sample carrier beyond the fixed registration elements; reversing the conveyor direction to back at least one of the sample carriers into contact with its corresponding registration elements; continuing to reverse the conveyor until all sample carriers are in contact with their respective registration elements; whereby the flexure elements of the sample carriers in contact with the respective registration elements will deform as the conveyor reverses to allow all sample carriers to contact their respective registration elements, thereby providing a known position of the sample carrier. The flexure device includes: first and second legs forming a inverted U-shape; a third leg which extends away from the top of the inverted U-shape; and a fourth leg which extends down the center of the U in the direction of the ends of the U.

2 Claims, 7 Drawing Sheets

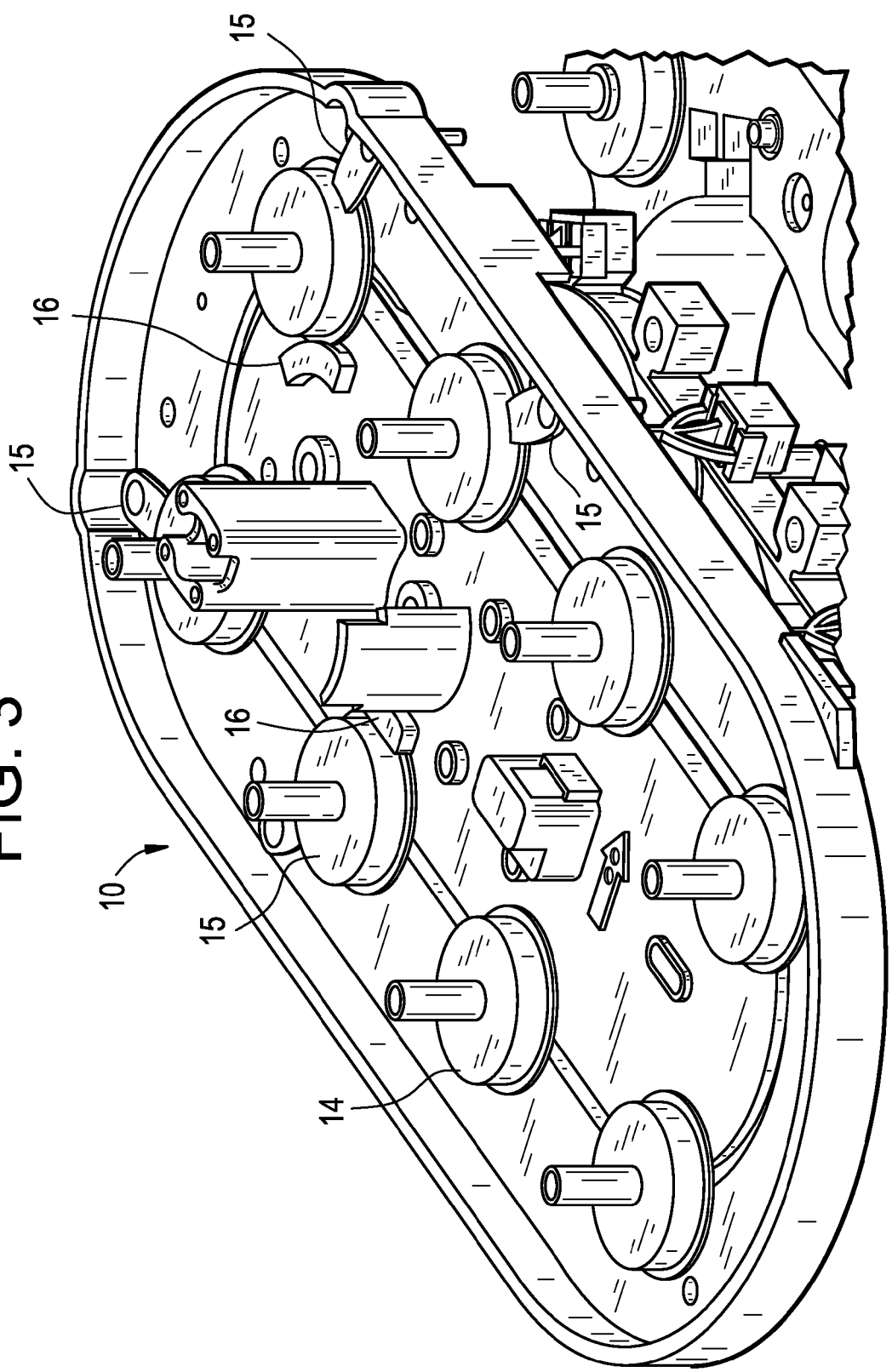

FIG. 5
FIG. 6
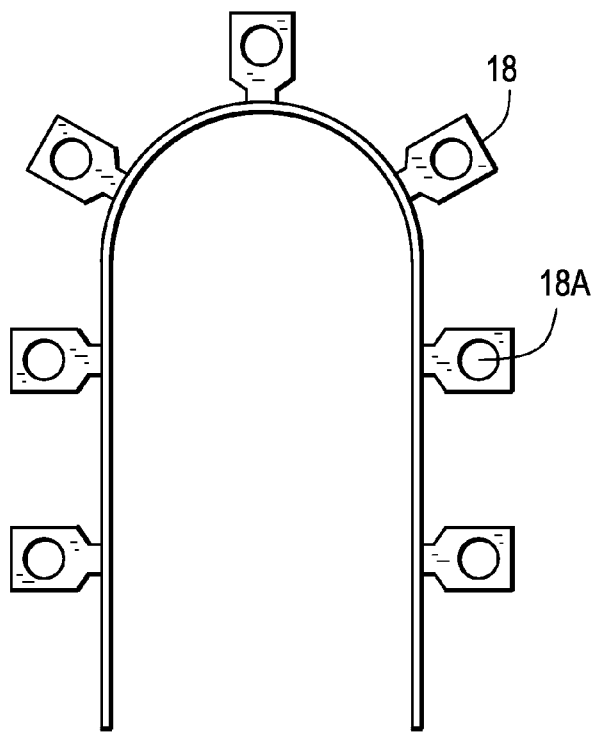
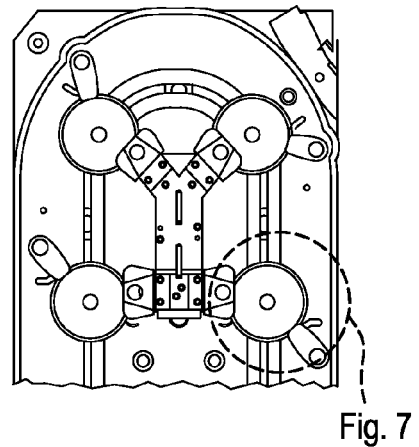
FIG. 7
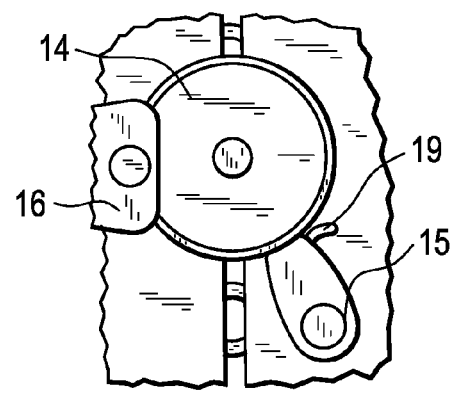

TWO DIMENSIONAL SAMPLE HANDLER

CROSS REFERENCE TO RELATED APPLICATIONS

This patent application is a divisional of U.S. Non-Provisional Application Ser. No. 11/672,614, filed Feb. 8, 2007, which granted on Jan. 11, 2011 as U.S. Pat. No. 7,867,768, the disclosures of which are incorporated by reference in their entirety.

BACKGROUND OF THE INVENTION

The present invention relates to sample handling in an automated diagnostic analyzer. In particular, the present invention relates to two dimensional sample handling in an automated diagnostic analyzers to allow greater access to a larger number of samples.

Known diagnostic analyzers include immunodiagnostic analyzers such as the Vitros® ECi immunodiagnostic analyzer, or clinical chemistry analyzers such as the Vitros® 5,1 FS, both sold by Ortho-Clinical Diagnostics, Inc. All such analyzers are collectively called diagnostic analyzers. Representative systems are disclosed for example in U.S. Published Patent Application No. 2003/0026733 and in U.S. application Ser. No. 10/684,599 filed Oct. 14, 2003, both of which are incorporated herein by reference in their entireties. Such systems have sample handling systems. For example, in the '733 publication a sample handler 14 has sample trays 18 (also called sample carriers), which contain individual sample containers, such as test tubes. The sample handler transports the sample trays on a belt (not shown) under metering transport rail 26 along a straight path, where metering truck 30 containing a sample aspirate/dispense probe will aspirate sample out of the individual sample containers. The sample trays 18 are shown in more detail in FIG. 3 of the '599 application. The sample tray (or sample carousel) 220 sits atop sample tray transport 210 which is either magnetically transported or is transported by a belt system in an elliptical path to a sample aspirate station 230 (see FIG. 1).

Both of these systems are constrained in that the metering probe can only access a single sample carousel at a time. This has the effect of slowing down the metering process. Also, it constrains the number of samples that can be accessed at single time. For example, if one carousel contains a sample being analyzed for HDL and another carousel also contains a sample also being analyzed for HDL only the first sample can be accessed. But, it would increase throughput to analyze both samples for HDL. However, for this to happen the sample transport would have to position the second carousel under the metering probe, hence slowing down the overall system speed.

One solution for accessing a greater number of sample carousels is to provide a metering probe that can move in two horizontal directions, thus allowing access to a greater number of sample trays and hence a greater number of samples. However, to ensure precise metering of sample, the sample and by definition the sample tray must be precisely registered in a predetermined position to ensure the metering probe will be able to properly access the sample container. In known systems, such as those described above, the sample tray is advanced past a fixed projection or registration stop. Once past, the sample tray is reversed and brought into a snug contact with the registration stop, thus providing proper registration. When more than one sample tray is to be registered, such as with the system shown in the '733 publication, i.e., one for the primary metering station and one for the reflex metering station, the trays are driven via the belt past their respective registration stops, the drive is then reversed and the trays registered against the registration stops. The flexibility of the direct drive belt, because of its length and distance from the drive pulley, insures both a proper loading tension and location for metering.

However, for systems requiring additional trays to be registered, the use of equivalent mechanical methods, such as the registration stop to register multiple sample trays simultaneously in more than one dimension would result in an over-constrained design (where the number of mechanical constraints would exceed the number of free parameters available). A system such as that described with respect to the '733 publication and the '599 application (i.e., registration is to be accomplished by reversing the drive direction and forcing the trays up against a registration stop), would require the tray transport to have a rigid coupling between trays and would subject the trays to higher than desired impact loads during registration.

Newer analyzer designs, such as shown in FIG. 1 employ multiple sample trays using a belt drive to move the trays from position to position where up to four of the sample trays can be registered at the same time. Given that the positional accuracy requirement of newer analyzers is the same as for analyzers known in the art, the use of equivalent mechanical methods to register four of the sample trays simultaneously would result in an over-constrained design (where the number of mechanical constraints would exceed the number of free parameters available). In a manner similar to the known analyzers, such as the ECi and 5,1FS analyzers described above, registration is to be accomplished by reversing the drive direction and forcing the trays up against a registration stop. This in turn would require the tray transport to have a rigid coupling between trays and would subject the trays to higher than desired impact loads during registration.

For the foregoing reasons, there is a need for a method of accessing a greater number of samples to allow greater throughput in the diagnostic analyzer. There is also a need to provide a system that will allow accurate registration of multiple sample trays.

SUMMARY OF THE INVENTION

The present invention solves the foregoing problem of accessing a greater number of samples to provide higher throughput in the diagnostic analyzer.

One aspect of the invention is directed to a method for positioning a sample in a diagnostic analyzer. The method includes: providing two or more sample carriers on a conveyor; providing a fixed registration element for each sample carrier at predetermined locations along the conveyor; providing a flexure device positioned between the sample carrier and the conveyor; advancing the sample carrier beyond the fixed registration elements; reversing the conveyor direction to back at least one of the sample carriers into contact with its corresponding registration elements; continuing to reverse the conveyor until all sample carriers are in contact with their respective registration elements; whereby the flexure elements of the sample carriers in contact with the respective registration elements will deform as the conveyor reverses to allow all sample carriers to contact their respective registration elements, thereby providing a known position of the sample carrier.

Another aspect of the invention provides a method for registering multiple objects on a conveyor in fixed positions, which includes: providing a conveyor having multiple objects thereon; providing fixed registration elements at predetermined locations along the conveyor; providing a flexure device positioned between the objects and the conveyor; advancing the objects beyond the fixed registration elements; reversing the conveyor direction to back at least one of the objects into contact with its corresponding registration elements; continuing to reverse the conveyor until all objects are in contact with their respective registration elements; whereby the flexure elements of the objects in contact with the respective registration elements will deform as the conveyor reverses to allow all objects to contact their respective registration elements.

Yet another aspect of the invention provides a flexure device which includes: first and second legs forming a inverted U-shape; a third leg which extends away from the top of the inverted U-shape; and a fourth leg which extends down the center of the U in the direction of the ends of the U.

Yet another aspect of the invention provides a sample handling system for a diagnostic analyzer which includes: a continuous belt; a flexure device as described above engaged with the continuous belt; a sample carrier movably engaged with the flexure element; registration elements arranged along the conveying system at predetermined locations; whereby when the sample carrier is transported beyond the fixed registration elements the conveyor direction is reversed such that at least one of the sample carriers comes into contact with its corresponding registration elements; and the conveyor is continually reversed until all sample carriers are in contact with their respective registration elements; where in the flexure elements of the sample carriers in contact with the respective registration elements will deform as the conveyor reverses to allow all sample carriers to contact their respective registration elements, thereby providing a known position of the sample carrier.

Further objects, features and advantages of the present invention will be apparent to those skilled in the art from detailed consideration of the preferred embodiments that follow.

BRIEF DESCRIPTION OF THE DRAWINGS

FIG. 3 shows a sample handler having eight sample tray transports according to a preferred embodiment of the present invention.

FIG. 5 shows a belt that the sample tray transport is transported on according to a preferred embodiment of the present invention.

FIG. 6 shows sample tray transport positioned against the registration elements in preparation for metering.

FIG. 7 is an expanded view of FIG. 6 showing that one of the sample tray transport is not registered against the registration element.

DETAILED DESCRIPTION OF PREFERRED EMBODIMENTS

While the present invention is described with respect to the preferred embodiment of registering samples in a diagnostic analyzer, the invention is applicable to any application where the registration of a multiple objects is necessary.

Figure 1:
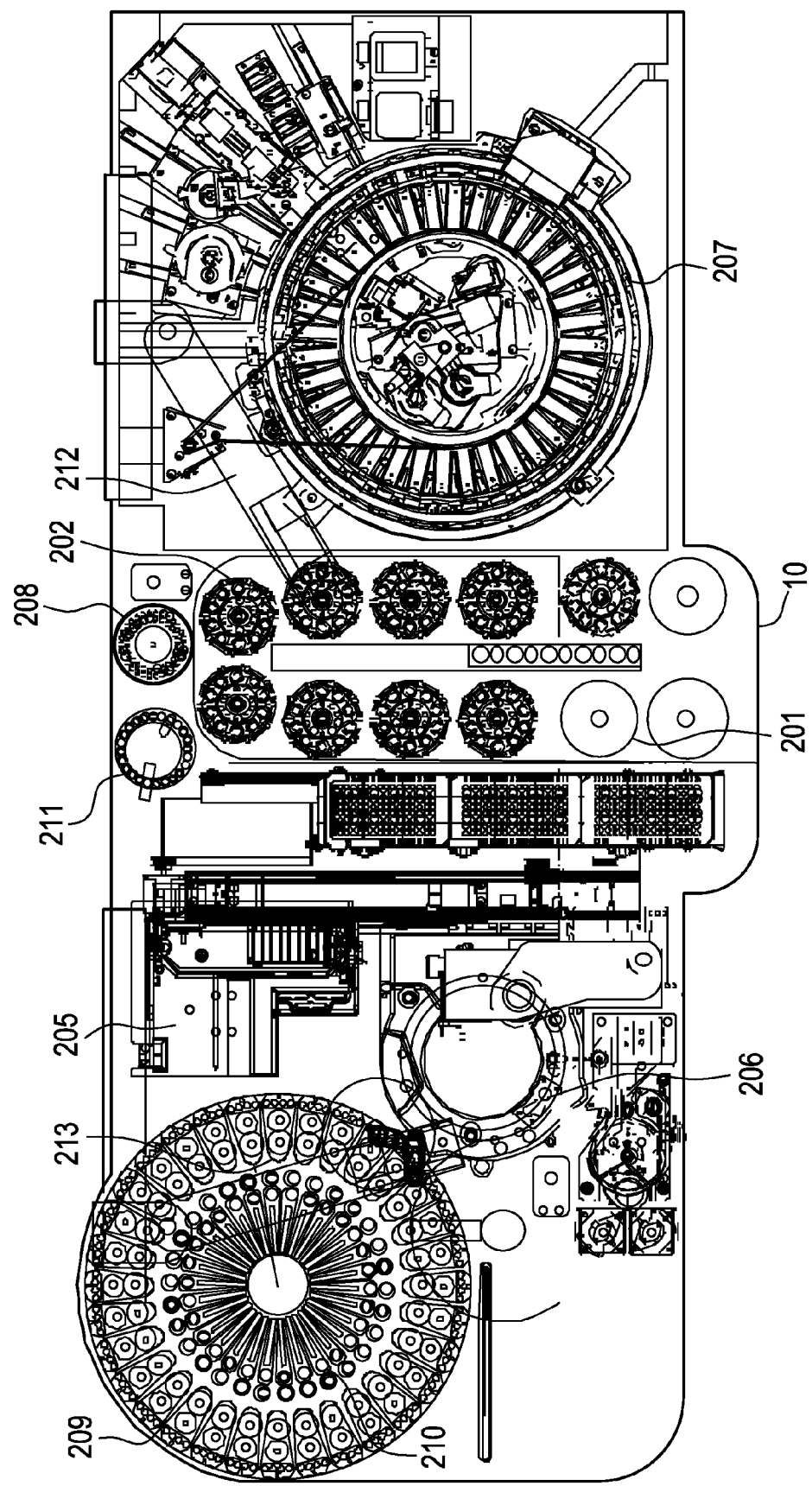
FIG. 1 is a schematic top view of a diagnostic analyzer that includes accessing samples in greater than one dimension.

FIG. 1 depicts the internal layout of the key components of a diagnostic analyzer according to a preferred embodiment of the present invention. The sample handler 10 is divided into two regions, the metering zone 202 and the operator load/unload zone 201. Contained within each zone is up to four sample trays 13 capable of holding up to ten individual samples. There are three chemistry zones, two wet chemistry zones 205 and 206, and a dry chemistry zone 207 which incubate and take measurements on the treated samples. Additionally, there are two reagent supply areas 209 and 210, a disposable tip supply area 208, and an aliquot buffer facility 211. Two robotic arms are contained in rack, one 212 having the capability to aspirate and meter samples by random access from any point in the metering zone to any one of the three chemistry zones, and the other 213 having the capability to aspirate and meter reagents by random access from any of the reagent supplies to any one of the three chemistry zones.

Figure 2:
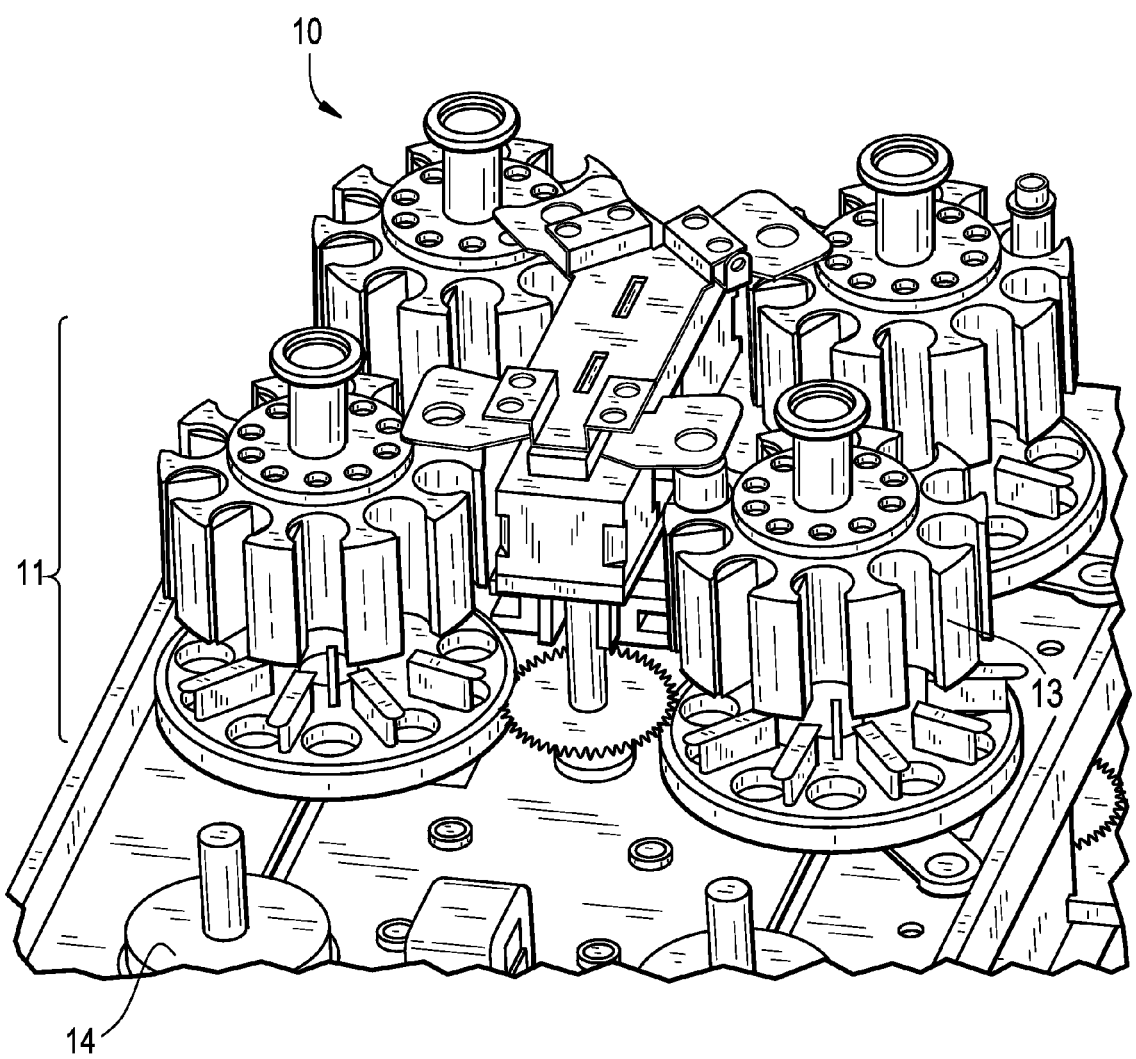
FIG. 2 shows four sample trays positioned for sample access in greater than one dimension according to a preferred embodiment of the present invention.
Figure 4A:
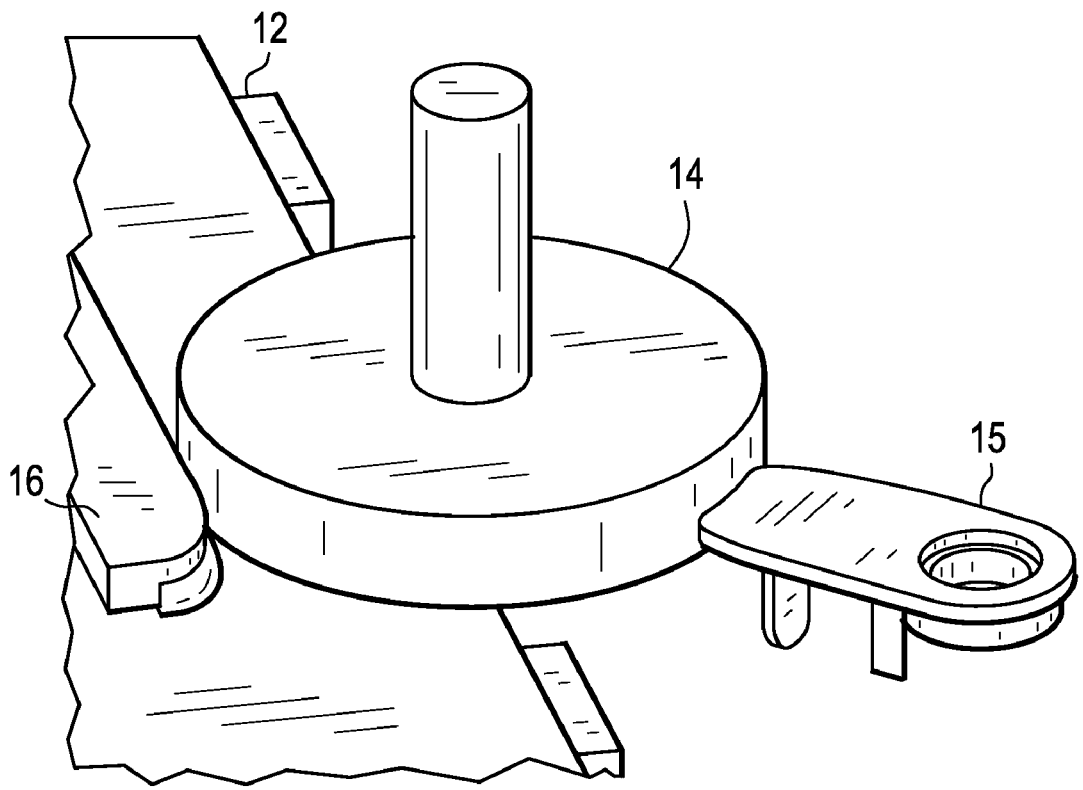
FIG. 4A shows a sample tray positioning according to a preferred embodiment of the present invention.
Figure 4B:
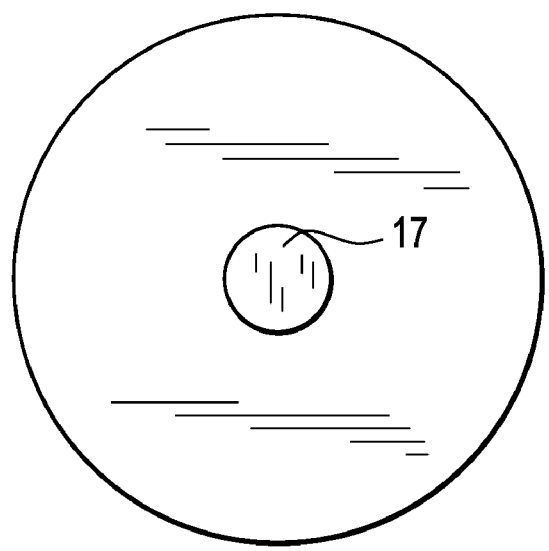
FIG. 4B shows the force vectors which act on the sample tray transport during the sample tray registration process.
Figure 8A:
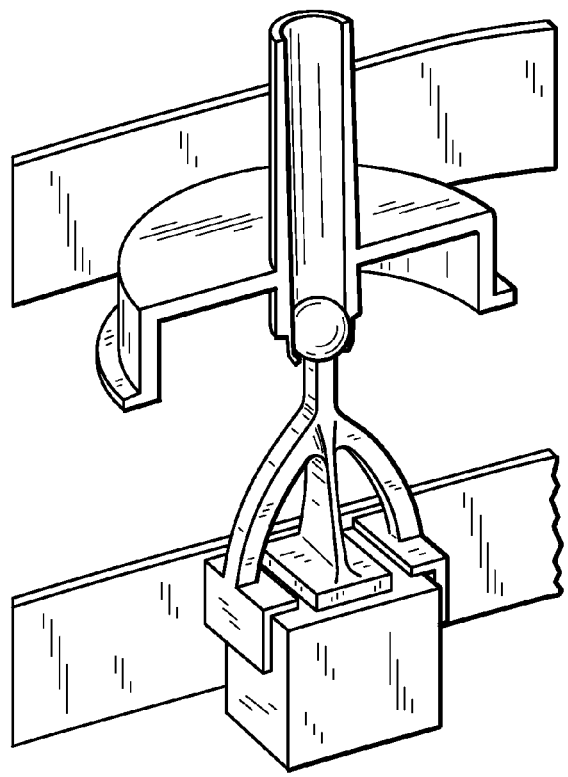
FIG. 8A shows a flexure device that is interposed between the sample tray transport and belt drive to provide enough flexibility to the conveyor system to allow all the sample trays to engage the registration elements according to a preferred embodiment of the invention.

FIGS. 2 and 3 show a sample handler 10 on a diagnostic analyzer, such as that described above. Sample handler 10 includes a sample carrier 11 and conveyor belt 12 (FIG. 8). Sample carrier 11 further includes sample tray or carousel 13, which sits atop sample tray transport 14, which in a preferred embodiment is a puck-shaped disk (FIGS. 3 and 4). The sample handler shown in FIG. 2 and FIG. 3 employ an array of input samples in two-dimensions. A preferred embodiment of the sample handler has eight sample carriers where four of the carriers are in the load/unload area and four of the sample carriers are in a metering area. In the FIG. 2 embodiment, the four carriers in the metering area are shown with the combined sample tray and sample container holder and two of the four carriers in the load/unload area are shown with only sample tray transport 14. In the FIG. 3 embodiment, the four sample tray transport are shown in the metering area with registration elements 15 and 16 described in more detail below. The sample tray transport is connected to the conveyor belt via flexure element 20 as shown in FIG. 8A and described in more detail below.

The sample carriers are driven from position to position by means of a belt drive 12. Up to four sample trays to be accessed by metering arm, described below, can be positioned or registered simultaneously. Thus, one aspect of the invention provides a method for registering multiple objects, preferably for positioning a sample in a diagnostic analyzer. Two or more sample carriers are provided on the conveyor. Preferably four sample carriers are provided. In another preferred embodiment, the sample carriers are rotary carriers capable of holding up to ten individual samples, such as sample test tubes. When four sample carriers are provided at all four metering positions the sample handler operates at its optimum, offering random access to as many as forty samples, allowing the analyzer to optimize the order of the samples, enabling multiple access points, and re-running any samples as needed.

The sample carriers are provided on a conveyor or index belt. To align the sample carriers in the metering position, the conveyor is rotated past fixed registration elements. In a preferred embodiment, the fixed registration elements include a movable flipper 15 and fixed registration wall 16 as shown in FIG. 3 and FIG. 4. Once the carriers are moved past the registration element, the conveyor is reversed resulting in the carrier contacting the registration elements 15 and 16. The reversal of the conveyor provides three force vectors acting through the center point 17 of the of the sample carrier. This convergence of vectors provides precise positioning of the sample carrier.

An important feature of the invention is the ability for all sample carriers to be aligned and positioned against registration elements. Prior to the present invention, if there was imprecision in the sample carrier assembly, for example the distance between lugs 18 (FIGS. 5 and 8A) on the conveyor belt was too small or too large, the sample carrier attached to the misaligned lug would fail to engage with the registration elements when the conveyor belt was reversed, resulting in misalignment of one or more of the sample carriers and hence misalignment of the sample tray. Due to the stiff connection between the sample carrier and the conveyor or index belt, when one or more of the sample carriers engage with the registration elements, the belt's motion will be stopped and the other sample carriers that are not aligned with the registration element will remain out of place. FIGS. 6 and 7 depict the misalignment of one sample tray transport, when the other three are aligned with the registration elements. Specifically, FIG. 6 shows three out of the four sample containers in alignment with their respective registration elements. FIG. 7 which is an expanded view of FIG. 6, shows the mis-registered sample tray transport. FIG. 7 clearly shows a gap 19 between the sample tray transport and the flipper-like registration element.

Figure 8B:
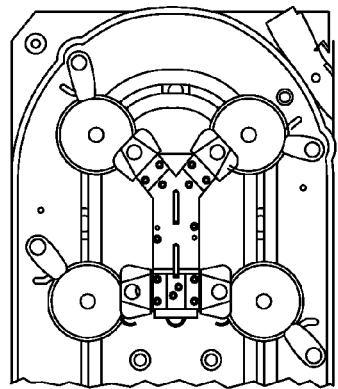
FIG. 8B shows four sample tray transports in registration with their corresponding registration element.
Figure 8C:
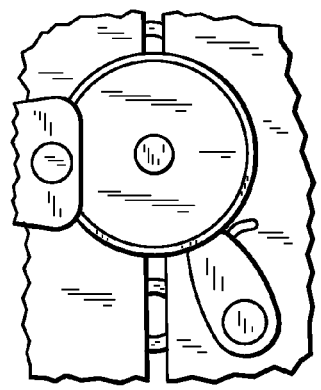
FIG. 8C is an expanded view of FIG. 8B showing an individual sample tray transport in registration with it corresponding registration element.

However, when flexure devices 20 are placed between the conveyor belt and the sample tray transports (FIG. 8A), the sample tray transport which is out of alignment with respect to the other sample tray transports, will continue to move when other sample tray transports have been stopped by the registration elements by virtue of the fact that the flexure device acts as a spring between the belt and sample container allowing continued movement of the belt and sample container into alignment with the registration element. FIGS. 8A-8C depict the correct alignment of all four sample containers. FIG. 8B shows all four sample tray transports 14 in contact with the registration elements including misaligned sample tray transport 14a. Exploded view FIG. 8C clearly shows the misaligned sample carrier holder in contact with the registration elements at the metering location.

Once the sample carriers are in the metering area the sample carriers are rotated in pairs. One pinion can rotate two trays. The barcode for each tray, and the tubes on the tray, are generally read in the first metering position. Once the bar code is read, the tray and tube identification are under analyzer control regardless of which metering position they are in.

In a preferred embodiment, the conveyor is a non-linear conveyor, preferably forming a continuous rectangular track such as shown in FIG. 1, having the registration elements and sample container holders evenly spaced around the track. In another preferred embodiment, the sample tray transports are puck shaped disks as shown in FIG. 8A having a socket on the bottom surface to engage with the flexure device and having an extension which extends perpendicular to the top surface of the sample tray transport and engage the sample trays.

The ability of a diagnostic analyzer to randomly access samples from multiple trays is one feature of this invention.

As described above, the ability to access samples in more than one dimension is made possible by aligning all the sample carriers on the conveyor belt. This in turn is achieved by the use of a flexure device between the sample carrier and the conveyor belt. Thus, an important aspect of the present invention is the use of a flexure device which is a mechanical component that flexes when required to provide compliance or "give" in the sample handling system. As described in connection with FIGS. 5-7, prior to the present invention, there was a problem of accurately aligning all sample carriers with their respective registration stops. If there was some imprecision in the placement of the sample carriers on the conveyor belt, e.g., the distance between a conveyor belt lug is to small or great, one or more of the sample carriers would be in registration with the registration stops before the other sample carriers. With this situation the force load on the carriers already in registration would increase as the conveyor belt continued to move in reverse to align the other carrier into registration with their respective registration elements.

The flexure device solves the problems of inflexible coupling of the sample carriers to the conveyor belt and the excessive impact load during registration that results. The flexure provides a mechanism for the registration forces to increase gradually by deforming the flexure device, thus eliminating the impact impulse generated when the sample carriers are pushed backward into the registration stop. It is also capable of providing the required sample carrier location accuracy by providing all sample trays in the metering position to be in registration with their respective registration elements.

The flexure device or element can be any suitable structure that is able to bend or deform in order to allow a conveyor belt to bring multiple objects on the conveyor belt into registration with their corresponding registration stops even if some objects being conveyed are somewhat misaligned, such as due to manufacturing tolerances.

In a preferred embodiment the flexure device includes first and second legs that form an inverted U-shape. Extending from the top of the inverted U is a third leg that extends upward to form with the U-shaped legs an inverted Y. The third leg is engaged with the object being conveyed, such as a sample carrier. A fourth leg extends downward from the top of the inverted U along the center of the U and in a direction toward the ends of the U. The fourth leg engages the conveyor belt transporting the object. In operation, when the object being conveyed is engaged with its respective registration stop, the third and fourth leg are able to bend such that the conveyor is able to continue its motion until the other objects are engaged with their respective registration stops. The first and second legs act as stops to the amount the third and fourth legs are allowed to bend.

In a preferred embodiment where the flexure device is engaged with block-shaped lugs, the first and second legs include inverted L-shaped brackets on the their ends. These L-shaped brackets engage the block-shaped lugs when the third and fourth legs deflect, limiting the range of deflection of the third and fourth legs. In another preferred embodiment, the second leg bifurcates into two additional legs that are frictionally engageable into a bore in the center of the legs. At the point of bifurcation is a flat surface that is perpendicular to the second leg and the two additional legs. This flat surface acts as a stop at the surface of the lug.

Figure 9:
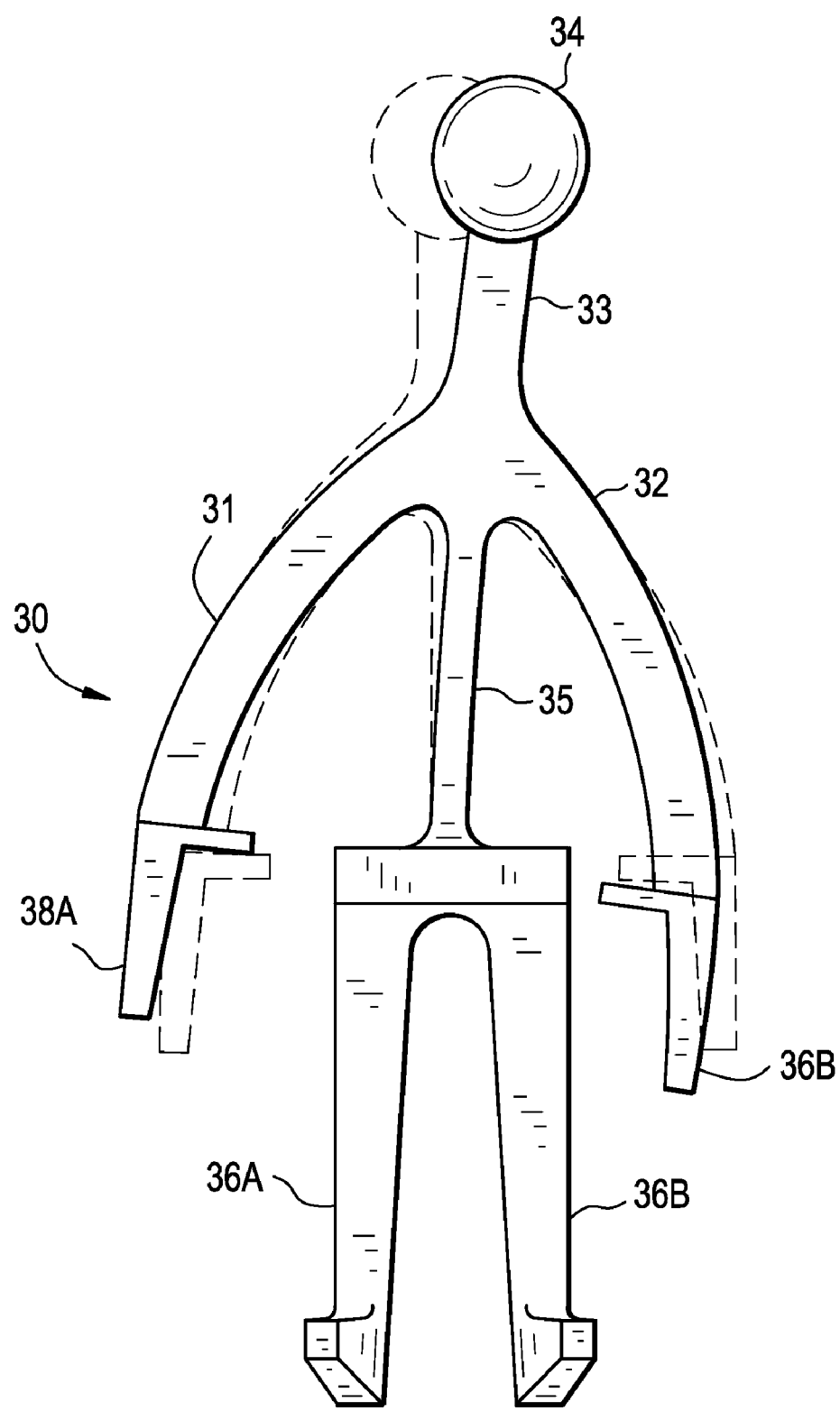
FIG. 9 shows the flexure device in a flexed position according to a preferred embodiment of the present invention.

FIG. 9 depicts a preferred embodiment of the flexure device. As shown FIG. 9, the flexure device 30 includes first and second legs 31 and 32 which form an inverted U-shape.

Extending upwardly from the top of the inverted U-shape is a third leg 33 that ends in ball 34. The third leg and its associated ball 34 engage the object being carried, such as the sample tray transport 14 (FIG. 8A) via socket 41. The flexure device also includes a fourth leg 35 extending downwardly from the top of the inverted U-shape. In the embodiment shown in FIG. 9, the fourth leg bifurcates into two prongs 36a and 36b. These prongs are adapted to frictionally engage a bore 18a in conveyor belt lug 18 into a snap-tight fit. When the prongs 36a and 36b are engaged in lug 18, flat surface 37 which is perpendicular to fourth leg 35 rests on the top surface of lug 18. The first and second legs also include at their ends, an inverted L-shaped brackets 38a and 38b.

In operation, the fourth leg 35 will flex and deform when lug 18 continues to move even after the top of the flexure device along with container holder 14 has contacted registration stops. The deformation will continue until the other container holders along the conveyor belt have contacted their registration stops, or until the L-shaped brackets 38a and 38b have contacted block 18, thus stopping any more deflection of leg 35. A preferred composition of the flexure device is Ticona Celcon M90™ Acetal Copolymer having the properties shown in Table 1.

| Hardness, Rockwell M | 80 | 80 | |
|---|---|---|---|
| Tensile Strength, Yield | 61 MPa | 8850 psi | |
| Elongation at Break | 60% | 60% | |
| Flexural Modulus | 2.6 GPa | 377 ksi | |
| Flexural Yield Strength | 90 MPa | 13100 psi | |
| Compressive Yield Strength | 110 MPa | 16000 psi | 10% Deflection; |
| Fatigue Strength | 28 MPa | 4060 psi | 10E+7 Cycles; |
| Shear Strength | 53 MPa | 7690 psi | |
| Izod Impact, Notched | 0.7 J/cm | 1.31 ft-lb/in | |
| Izod Impact, Notched Low Temp | 0.5 J/cm | 0.937 ft-lb/in | −29° C.; ASTM D256 |
| Tensile Impact Strength | 150 kJ/m$^2$ | 71.4 ft-lb/in$^2$ | |

The method for accessing samples in two-dimensions according to the present invention can be implemented by a computer program, having computer readable program code, interfacing with the computer controller of the analyzer as is known in the art.

It will be apparent to those skilled in the art that various modifications and variations can be made to the methods and product of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. A flexure device comprising:
   first and second legs forming an inverted U-shape;
   a third leg that extends away from the top of the inverted U-shape and includes a ball; and
   a fourth leg which extends down the center of the inverted U-shape in the direction of the ends of the inverted U-shape, inverted L-shaped brackets are attached to each of the legs forming the U-shape, and a flat surface element is attached to the fourth leg, wherein the flat surface is perpendicular to the fourth leg.

2. A sample handling system for a diagnostic analyzer comprising:
   a conveyor including a continuous belt having a plurality of block-shaped lugs;
   a flexure device comprising:
      first and second legs forming an inverted U-shape;
      a third leg that extends away from the top of the inverted U-shape and includes a ball; and
      a fourth leg which extends down the center of the inverted U-shape in the direction of the ends of the inverted U-shape, a flat surface element is attached to the fourth leg and the flat surface extends perpendicular to the fourth leg,
      inverted L-shaped brackets are attached to each of the legs forming the U-shape, wherein each inverted L-shaped bracket of the flexure device is attached to a block-shaped lug;
   a plurality of sample carriers, each sample carrier including a sample tray transport having a socket at the bottom movably engaged with the ball of the flexure element; and
   a plurality of registration elements arranged along the conveying system at predetermined locations;
   whereby when the sample carrier is transported beyond the fixed registration elements the conveyor direction is reversed such that at least one of the sample carriers comes into contact with its corresponding registration elements; and
   the conveyor is continually reversed until all sample carriers are in contact with their respective registration elements; wherein the sample carriers in contact with the respective registration elements will deform the flexure device as the conveyor reverses to allow all sample carriers to contact their respective registration elements, thereby providing a known position of the sample carrier.

* * * * *